United States Patent [19]

Moisdon

[11] Patent Number: 5,595,563
[45] Date of Patent: Jan. 21, 1997

[54] METHOD AND APPARATUS FOR MAINTAINING THE POSITION OF BODY PARTS

[76] Inventor: Roger G. F. Moisdon, 4875 SW. 28th Ave., Fort Lauderdale, Fla. 33312

[21] Appl. No.: 523,265

[22] Filed: Sep. 5, 1995

[51] Int. Cl.⁶ .................................................. A61M 13/00
[52] U.S. Cl. ............................... 600/12; 606/61; 128/899
[58] Field of Search ........................... 606/61, 60, 105; 128/899; 600/12; 446/129

[56] References Cited

U.S. PATENT DOCUMENTS

| 4,029,091 | 6/1977 | Von Bezold et al. |
|---|---|---|
| 4,197,840 | 4/1980 | Beck et al. |
| 4,328,245 | 5/1983 | Harrigan ................................ 446/129 |
| 5,165,347 | 11/1992 | Wagner ................................. 446/129 |
| 5,219,349 | 6/1993 | Krag et al. ............................... 606/61 |

OTHER PUBLICATIONS

Publ. Oral and Maxillofacial Surgery Clinics of North America, vol. 6, No. 2, May 1994, "Indications for Surgical Treatment of Internal Derangements of the Temporomandibular Joint".

Publ. Oral and Maxillofacial Surgery Clinics of North America, vol. 7, No. 1, Feb. 1995, "Bite Appliance Therapy for Myofascial Pain and Dysfunction".

Primary Examiner—Michael Powell Buiz
Assistant Examiner—Mark S. Leonardo
Attorney, Agent, or Firm—Herbert L. Lerner; Laurence A. Greenberg

[57] ABSTRACT

A method for maintaining the normal position of body parts includes attaching a positioning device to opposite sides of body parts abnormally approaching each other too closely. The positioning device is adjusted for repositioning the body parts to a normal position. An apparatus for maintaining the normal position of body parts includes a positioning device to be placed in the vicinity of opposite sides of body parts abnormally approaching each other too closely. The positioning device is fixed in place relative to the body parts. The positioning device is adjustable for repositioning the body parts to a normal position. The apparatus may be used in combination with body parts.

42 Claims, 8 Drawing Sheets

METHOD AND APPARATUS FOR MAINTAINING THE POSITION OF BODY PARTS

BACKGROUND OF THE INVENTION

1. Field of the Invention

The invention relates to a method and an apparatus for maintaining the position of body parts, which can be accommodated to several different applications to fit a patient's health care needs.

The main health problem which is related to the present invention is mostly caused by any abnormal pressure of the bones exerted on the related cartilage. Mechanical and magnetic devices are interchangeable in their applications, and are used according to the needs of the patient and to the acceleration rate of the related therapy.

For example, during a pre-surgery period, one of the mechanical devices could be used to relieve the patient from pain and then the magnetic devices could be used to provide a constant therapy application mode.

The therapy related to the present invention is based on an easy return of the body parts to their natural integrity, functions and normality.

The difference between the two therapies is that the state-of-the-art therapy very seldom allows full recovery and full return to total normal comfort, besides being very expensive.

The therapy of the present invention, by acting gently and constantly for as long as necessary, in comfort and security, allows a full recovery of the body parts, in a natural way to a full restoration and may realign bones and joints, which cannot be done by the therapy according to the state of the art.

Besides congenital deficiencies, diseases such as arthritis, arthrosis or accidents can be a cause of bone displacement which, in turn, can aggravate orthopedic problems such as synovial extravasation and cartilage destruction, and can even require joint replacement.

DESCRIPTION OF THE RELATED ART

The state of the art related to the above-mentioned cases mostly uses the following techniques: elongations, massages, chiropractic manipulations and injections, etc. provide little or no permanent improvement for the patient. The main reason for the lack of permanent improvements is that the state of the art technology has no way to control and permanently maintain the position of the displaced bones after the above-mentioned techniques have been applied. Quite often, besides the pain, the patient's relief does not last.

For example, a bone which is placed back in its socket slips out again, right after the chiropractic manipulation, when the doctor is no longer there to set it back again.

The most damaging effect of the above-mentioned methods is that they are applied during a short time period, and with a great deal of force. Generally, bone displacements take a long time to occur, and setting them back in a short period of time causes too much trauma.

Another example is a case of arthrosis of the knee, in which a related disabled cartilage is naturally squeezed between the femur and the tibia, and consequently subjected to the rubbing force of the two bones, which is the consequence of the permanent and natural pulling of the related soft tissues. The cartilage, having lost its elasticity, causes some of its chondrocyte cells to be flattened and since they no longer accept the necessary nutriments, they decay and disappear. The cartilage becomes flattened too, and ultimately disappears. Then the femur and the tibia are in contact and rub against each other, with the pain and cracks associated with a disabled knee. The state of the art remedy is firstly a surgically implanted curved plaque on which the two bones will rub without the benefit of the hyaline cartilage and secondly, or in extreme cases, a joint replacement, with all of the difficulties and suffering involved.

A further example is that of casts which are cumbersome, uncomfortable, dirty, and cause ankylosis, loss of muscular mass, and create a need for rehabilitation, which is painful and costly. Moreover, it is to be understood that casts are not usable everywhere, although magnetic implants are.

It is accordingly an object of the present invention to provide a method and an apparatus for maintaining the position of body parts, which overcome the hereinaforementioned disadvantages of the heretofore-known methods and devices of this general type and which provide a new surgical technique that is capable of permanently controlling the relative position of the bones and other parts found in living bodies by mechanical adjustments as well as by adjustable magnetic position devices, that are capable of painlessly integrally restoring any joints to their natural origin and functions, immediately after implantation of the components of the device, with a faster, improved, natural healing process.

The surgery associated with such a new technique allows much more flexibility and comfort for the patient as well as for the surgeon. In fact, long hours of surgery are no longer needed, since the implantation of the magnetic devices can be performed routinely in a relatively short time, and the time-consuming adjustments can be made any time thereafter, without any more surgery at the doctor's office by a nurse or by the patient himself, according to his personal rate of healing, and according to his feeling and comfort.

The laws of physics provide two different methods for achieving a task. The task may be achieved first during a short period of time, under a large amount of power, and second during a long period of time, under a small amount of power.

The first method is exclusively used by the therapy according to the state of the art. The second method is exclusively used by the type of therapy according to the present invention.

Healing takes time; with the first method it can never be achieved, but with the second method not only can it be achieved but the healing time is not harsh because the magnetic field restores the joint functions immediately or soon after surgery. An interesting feature of the magnetic dispositions of the devices used in the present invention is based on a physical law stating that a magnetic field variation between two magnets is always increasing or decreasing according to the inverse of the square of the linear distance variation existing between the two magnets. Such a device becomes a first class shock absorber since the above law states that the closer the two magnets get, the stronger their magnetic repulsion becomes (carried to the square).

It is generally accepted in the medical profession that the reason for a cartilage to decay is poor nourishment because such cartilage is without an integral blood supply. Evidently, if that were the case, everyone on earth would experience decaying cartilage. Since only a percentage of humans experience such a decay, the lack of blood supply cannot be the cause. Very probably, injuries and disease are the plausible causes.

In quite the opposite way, the use of the positioner has demonstrated a strong proclivity of the cartilage to regenerate when relieved from the pressure of the bones. If a sound cartilage is capable of withstanding very high bone pressure, an injured or diseased one is not, having lost some of its natural elasticity and strength, but with the pressure of the bones remaining constant, the decay of such cartilage is inevitable and cartilage cells become flattened and cannot diffuse the nutrients and waste from vessels in the perichondrium or fluid in the joint space, with the result being the disappearance of a part of the cartilage and friction of the bones against each other.

Contrary to the natural cartilage which can be destroyed by injuries or diseases, the magnetic implants can take a lot of punishment and stay unaffected by it or by any diseases or pressure.

Therefore, a magnetic implant device in fact acts as a nursing device, consolidating and preserving a particular joint against eventual similar injuries or against other types of injuries. This type of protection can be used as preventive care and for protection, for example, against repeated sports or occupational injuries, or risks of dislocations due to specific diseases.

During several years, experiments have been made on human fingers, with rudimentary models of mechanical positioners. Such experiments have revealed that:

1. there is no need for a strong repulsive power on disabled joints to set the bones back in their correct location; and
2. a small repulsive power, relieving only a little of the normal pressure, is enough for the injured cartilage to regenerate.

The experiments were fully satisfactory, and no recurrence has been experienced, yet bone enlargements have been resorbed.

It is thus an object of the present invention to provide a new method of therapy for prompt restoration of functions of body parts, in comfort and security, which are qualities that are lacking in the state of the art therapy.

It is a further object to provide some of the necessary medical apparatus for the implementation of the therapy object of the present invention.

It is still a further object to provide some medical tools necessary for the adjustment of such apparatus, and magnetic power delivery.

The law on which the present invention is based may be stated as follows: The magnetic forces existing between the poles of two magnets are inversely proportional to the square of the linear distances defining an interspace therebetween.

The above and even further objects and advantages of the present invention will become apparent in the hereinafter set forth detailed description of the invention, the drawings and claims appended herewith.

With the foregoing and other objects in view there is provided, in accordance with the invention, a method for maintaining the normal position of body parts, which comprises attaching a positioning device to opposite sides of body parts abnormally approaching each other too closely, and adjusting the positioning device for repositioning the body parts to a normal position.

In accordance with another mode of the invention, there is provided a method which comprises attaching magnets of the positioning device to the opposite sides of at least two body parts.

In accordance with a further mode of the invention, there is provided a method which comprises orienting north and south poles of the magnets relative to each other, for repositioning the body parts.

In accordance with an added mode of the invention, there is provided a method which comprises inserting temporarily magnetizable material of the positioning device into the opposite sides of at least two body parts, and approaching the material with a magnetizer, for repositioning the body parts.

In accordance with an additional mode of the invention, there is provided a method which comprises placing the magnets into implantable containers, and attaching the containers to the body parts.

In accordance with yet another mode of the invention, there is provided a method which comprises placing the magnets in magnetic sleeves, attaching the magnetic sleeves to the body parts, and rotating the magnets in the magnetic sleeves.

In accordance with yet a further feature of the invention, there is provided a method which comprises pressing an at least partly magnetic latch into a hole formed in the bottom of one of the magnets with a spring disposed between the bottom of one of the containers and the bottom of the magnet, and approaching the latch with a magnetic tool causing the latch to exit the hole and freeing the magnet for rotation.

In accordance with yet an added mode of the invention, there is provided a method which comprises attaching magnets of the positioning device to opposite sides of a foot, orienting north and south poles of the magnets towards each other on one side of the foot and away from each other on the other side of the foot, for repositioning the body parts.

In accordance with yet an additional mode of the invention, there is provided a method which comprises implanting rod-shaped magnetic positioners into adjacent vertebrae, and adjusting the position of the magnetic positioners with a wrench, for repositioning the body parts.

In accordance with again another mode of the invention, there is provided a method which comprises implanting sheet magnets at ends of bones in a joint in a mutually repulsive position, for repositioning the body parts.

In accordance with again a further mode of the invention, there is provided a method which comprises implanting disk-shaped magnets into chambers formed in adjacent vertebrae in a mutually repulsive position, for repositioning the body parts.

In accordance with again an added mode of the invention, there is provided a method which comprises implanting sleeve-shaped magnets into a body part with like poles of the magnets facing each other in a self-centering, mutually repulsive position, for repositioning the body parts.

In accordance with again an additional mode of the invention, there is provided a method which comprises attaching an arm to a bone at a fulcrum, attaching a first magnet to the arm, attaching a second magnet to a body part to be controlled, and placing the magnets near each other, for repositioning the body part.

In accordance with still another mode of the invention, there is provided a method which comprises supporting a first magnet on a muscle, and attaching a second magnet to a body part in the vicinity of the first magnet with like poles of the magnets facing each other, for repulsing the second magnet with the first magnet when the muscle is contracted.

In accordance with still a further mode of the invention, there is provided a method which comprises placing magnetic rings over a limb on opposite sides of a joint in the limb, and adjusting relative circumferential positions of the rings causing the rings to attract or repel each other, for repositioning the limb.

In accordance with still an added mode of the invention, there is provided a method which comprises placing a base over a limb on one side of a joint in the limb, attaching one end of a spring to the base, attaching another end of the spring to the limb on an opposite side of the joint, and coiling the spring to produce a desired force, for repositioning the limb.

In accordance with still an additional mode of the invention, there is provided a method which comprises curving one end of a spring around a base of a limb, passing another end of the spring through a nail on the limb, and adjusting coils of the spring around the limb, for repositioning the limb.

With the objects of the invention in view, there is also provided an apparatus for maintaining the normal position of body parts, comprising a positioning device to be placed in the vicinity of opposite sides of body parts abnormally approaching each other too closely, and means for fixing said positioning device in place relative to the body parts, said positioning device being adjustable for repositioning the body parts to a normal position.

In accordance with another feature of the invention, the positioning device includes magnets to be attached to the opposite sides of at least two body parts.

In accordance with a further feature of the invention, the magnets have north and south poles being oriented relative to each other, for repositioning the body parts.

In accordance with an added feature of the invention, the positioning device includes temporarily magnetizable material being inserted into the opposite sides of at least two body parts, and a magnetizer approaching said material, for repositioning the body parts.

In accordance with an additional feature of the invention, the positioning device includes implantable containers surrounding said magnets and being attached to the body parts.

In accordance with yet another feature of the invention, the positioning device includes magnetic sleeves surrounding said magnets and being attached to the body parts, said magnets being rotatable in said magnetic sleeves.

In accordance with yet a further feature of the invention, there is provided an at least partly magnetic latch, a spring disposed between a bottom of one of said containers and a bottom of one of said magnets for pressing said latch into a hole formed in said bottom of said magnet, and a magnetic tool causing said latch to exit said hole upon approaching said latch, for freeing said magnet for rotation.

In accordance with yet an added feature of the invention, the positioning device has magnets and brackets fastened to said magnets for attaching said magnets to opposite sides of a foot with north and south poles of said magnets being oriented towards each other on one side of the foot and away from each other on the other side of the foot, for repositioning the body parts.

In accordance with yet an additional feature of the invention, the positioning device includes rod-shaped magnetic positioners to be implanted into adjacent vertebrae, and a wrench for adjusting a position of said magnetic positioners, for repositioning the body parts.

In accordance with again another feature of the invention, the positioning device includes sheet magnets to be implanted at ends of bones in a joint in a mutually repulsive position, for repositioning the body parts.

In accordance with again a further feature of the invention, the positioning device includes disk-shaped magnets to be implanted into chambers formed in adjacent vertebrae in a mutually repulsive position, for repositioning the body parts.

In accordance with again an added feature of the invention, the positioning device includes sleeve-shaped magnets to be implanted into a body part with like poles of the magnets facing each other in a self-centering, mutually repulsive position, for repositioning the body parts.

In accordance with again an additional feature of the invention, there is provided an arm to be attached to a bone at a fulcrum, a first magnet attached to said arm, and a second magnet to be attached to a body part to be controlled, said magnets being placed near each other, for repositioning the body part.

In accordance with still another feature of the invention, there is provided a first magnet to be supported on a muscle, and a second magnet to be attached to a body part in the vicinity of said first magnet with like poles of said magnets facing each other, for repulsing said second magnet with said first magnet when the muscle is contracted.

In accordance with still a further feature of the invention, there are provided magnetic rings to be placed over a limb on opposite sides of a joint in the limb and circumferentially adjusted in position causing said rings to attract or repel each other, for repositioning the limb.

In accordance with still an added feature of the invention, there is provided a base to be placed over a limb on one side of a joint in the limb, a spring having one end attached to said base and another end to be attached to the limb on an opposite side of the joint, said spring being coiled to produce a desired force, for repositioning the limb.

In accordance with a concomitant feature of the invention, there is provided a spring having one end being curved around a base of a limb, another end being passed through a nail on the limb and coils being wrapped around the limb and adjustable, for repositioning the limb.

The apparatus for maintaining the normal position of the body parts may be in combination with the body parts.

Other features which are considered as characteristic for the invention are set forth in the appended claims.

Although the invention is illustrated and described herein as embodied in a method and an apparatus for maintaining the position of body parts, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1A:
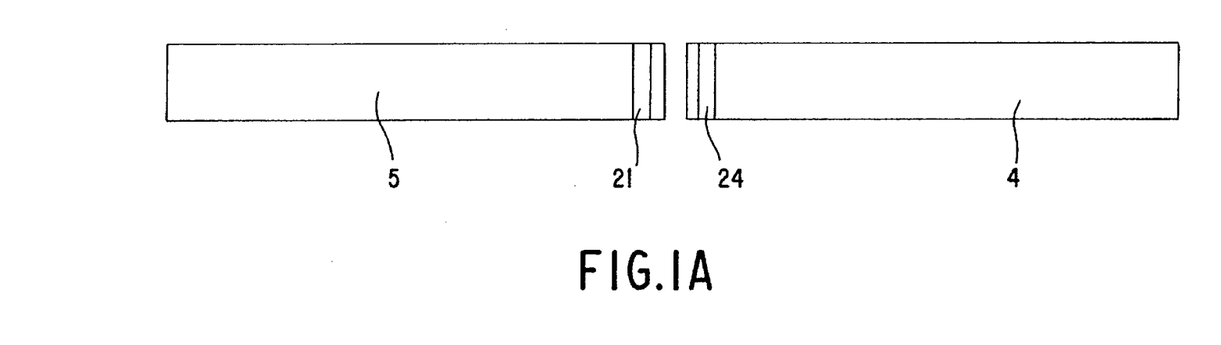
FIG. 1A is a diagrammatic, elevational view illustrating the basic concept of the invention.

Referring now to the figures of the drawing in detail and first, particularly, to FIG. 1A thereof, there are seen elements 4 and 5 which represent bones approaching each other in any joint within parts of the human body. Due to deterioration of the joint, the bones may approach each other too closely or may even come into contact with each other. According to the basic concept of the invention, magnets 21 and 24 are inserted into respective holes formed in opposite sides of the elements 5 and 4 in order to maintain the original position of the elements within the body parts.

Figure 1B:
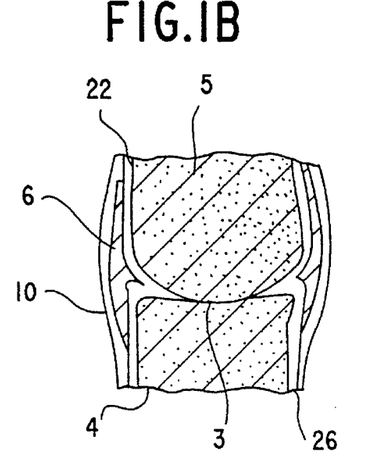
FIG. 1B is a fragmentary, cross-sectional view of a disabled knee joint.
Figure 1C:
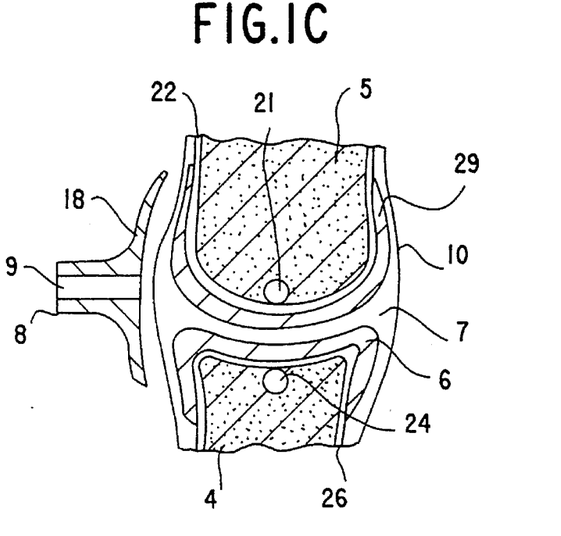
FIG. 1C is a view similar to FIG. 1B, in which a magnetic positioner according to the invention has been installed.

FIGS. 1B and 1C are cross-sectional views showing two bones such as a tibia 4 and a femur 5 in a knee joint 10. Soft tissue 6, 29, a hyaline cartilage 7 which is depicted as a meniscus cartilage, other soft tissue 22 which is a plate of cartilage covering the femur 5 and further soft tissue 26 which covers a top part of the tibia 4, are also shown.

In FIG. 1B the joint 10 is disabled having lost the most important part of its cartilage so that the bones touch each other at their boundaries 3. In FIG. 1C, a magnetic positioner in the form of two adjustable magnets 21–24 being magnetized across the diameter, is implanted in the joint 10. The magnet 21, for example, is implanted through the use of a drilling template 8 having a drilling guide 9 and a hat-peg or contact base 18 assuring accurate drilling for positioning the magnet.

The cylindrical magnets 21–24 are rotatably adjustable, in order to vary their magnetic field intensity from 0 to 100% and from repulsion to attraction, and vice versa.

In the joint 10 of FIG. 1C, the soft tissues 29, 6 and the cartilage 7 are healthy and the bones 4 and 5 are normal. The soft tissues 22 and 26 are intact. Two magnets 21–24 have been implanted by placing the contact base 18 of the template 8 on the side of the knee joint 10 and drilling through the guide 9.

A comparison of FIG. 1B with FIG. 1C shows that in FIG. 1B the disabled joint 10 has been represented by showing a lower extremity of a femur bone 5 in intimate contact with an upper extremity of a tibia bone 4. The soft tissues 22 and 26 of each bone are worn away at their boundaries 3. There is no longer any fibrocartilage or meniscus 7 remaining. Reference numeral 6 indicates a remnant of a plate of cartilage normally covering the articular surface of each of the bones 4 and 5.

A view of the medical situation of the joint 10 in FIG. 1B makes it clear that no healing process can take place as long as the two bones remain in contact or are too close, because the cells of the soft tissues between them have been permanently compressed and cannot be healed. If the two bones can be repositioned close to their original locations and permanently kept at such original position, then the healing process could take place and not be impaired again. This means that the joint would remain free from such a disease for life. The magnetic cushion formed by the magnetic repulsion taking place between the two bones reinforces the natural elasticity of the related cartilage, and prevents any accidental contact between bones.

In order to fulfill the principal object of the present invention, which is to provide a therapeutic positioning of bones by using the magnetic positioner, the two magnets 21 and 24 are oriented until a suitable repulsive force is obtained and then the two magnets are locked in such a position.

In the event that another injury causes another change in the position of those two bones, a non-surgical magnetic adjustment is made with the help of magnetic tools, and the object of the present invention is continued to be met.

Experiments conducted by the inventor of the present invention have shown that the state-of-the-art therapy is wrongly based on the assumption that common diseases are the original cause of bone and soft tissues destruction, when it is actually trauma inflicted at any age that opens the way for diseases to destroy an otherwise healthy joint. Moving the bones back into their correct position allows diffusion of nutriments everywhere they are needed for a full restoration.

Figures 2, 18:
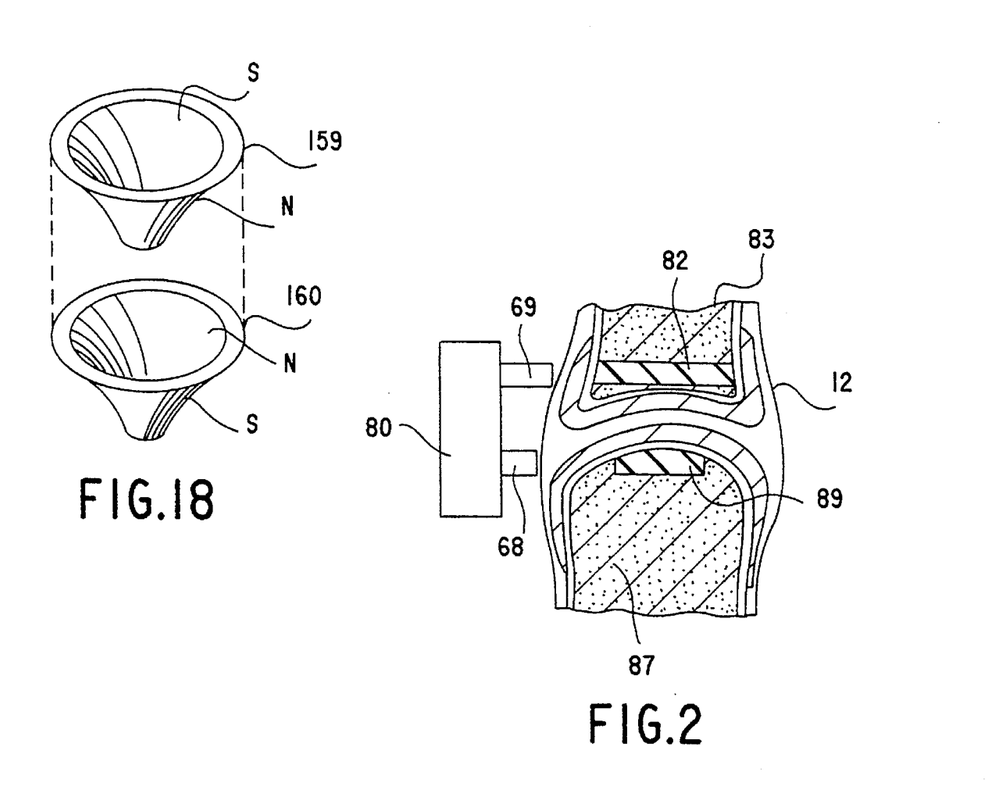
FIG. 2 is a fragmentary, cross-sectional view of a knee joint in which two magnetic devices have been installed.
FIG. 18 is an exploded, perspective view of two automatically centering positioning devices.

FIG. 2 shows a knee joint 12 in which a bone 83 is fitted or implanted with a magnetic mass 82 and a bone 87 is fitted or implanted with a magnetic mass 89. The two neutral magnetic masses 82, 89 are magnetized by placing an electromagnetizer 80 on the side of the joint 12 in a like-poles mode, so that two like poles are disposed one above the other, in the position shown in the figure.

A magnetic field produced by the magnetizer 80 is transmitted or driven to the two masses 82, 89 by two lengthwise adjustable tongues 68, 69, which are placed over two corresponding ends of the masses 82, 89 with the polarity being suitable to provide like poles for repulsion or opposite poles for attraction. When electric power is switched on, the magnetic field carried by the two tongues 68–69 is absorbed by the magnetic masses 82, 89, causing the masses to either repulse or attract each other with a strong force, which is controllable by varying the intensity of the magnetic field emitted by the magnetizer 80. Among other benefits and uses, this device can be used for new therapies or endoscopic examination and evaluation.

Figure 3:
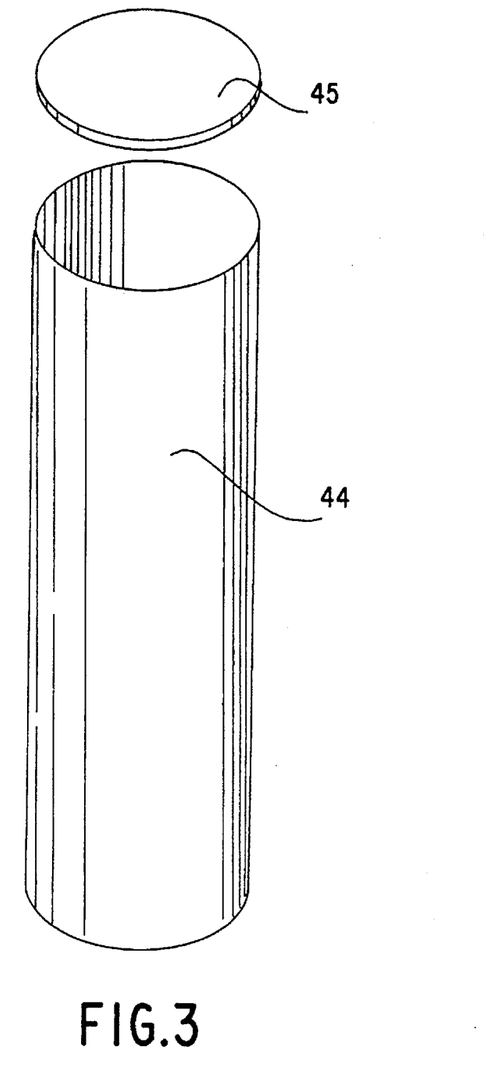
FIG. 3 is an enlarged, exploded, perspective view of an implantable magnet container.

FIG. 3 illustrates an implantable container 44 having a lid 45 for air-tight containment of magnetic devices. The container 44 may be used for the elements 21 and 24 of FIG. 1C.

Figure 4:
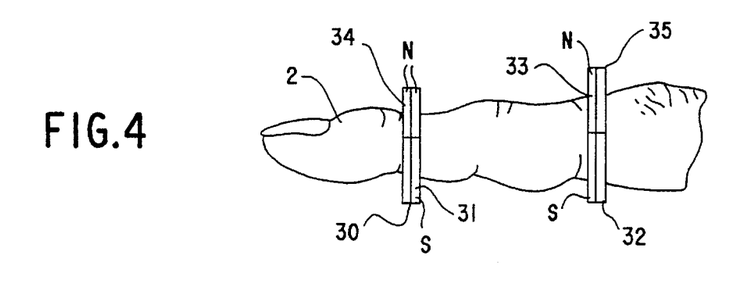
FIG. 4 is a fragmentary, side-elevational view of a ring magnetic positioner device on a human finger.

As is illustrated in FIG. 4, a human finger 2 is fitted with four halves of thick, washer-like magnetic rings 31, 32, 33, 34 being magnetized through their thickness and assembled in a two by two mode, in which north poles bearing reference symbol N and south poles bearing reference symbol S are opposite one another.

The magnetic positioner depicted in FIG. 4 has a closed magnetic field with a north pole associated with a south pole on one surface. It is noted that the same positioner device may be assembled with a unique pole north or south on one surface; but as a result, the magnetic repulsion/attraction would not be controllable and the general orientation of the push or pull would not exist, since the push or pull would be uniform.

In order to prevent sliding of the two magnetic rings 31, 34 and 32, 33 over the finger 2, inner surfaces of the rings which are in contact with the finger 2 are roughened or are covered by a sticky substance providing enough friction with the skin to ensure that they will not turn around freely. At one given position of the rings on the finger 2, they repulse each other by 100%. At a diametrically opposed position, they attract each other by 100%. Any intermediary positions will provide a percentage of their magnetic field attraction or repulsion and consequently a suitable amount of repulsion can be obtained in this way and positioning can be facilitated by marks imprinted on the rings. The rotation of one ring would be enough to adjust the amount of repulsion or attraction between the two rings.

The magnetic rings are grooved around their circumference for fastening, such as with rubber bands 30, 35, for example. The two rings, which may be composite magnetic rings, are assembled and maintained as such by the fastener or rubber bands that are placed into the grooves 30 and 35. As is seen in FIG. 4, the ring 31, 34 is placed behind a first joint of the finger 2 and the ring 32, 33 is placed over the front part of a second phalange, in order to push against it and separate the bones of the second and third phalange.

Figure 5:
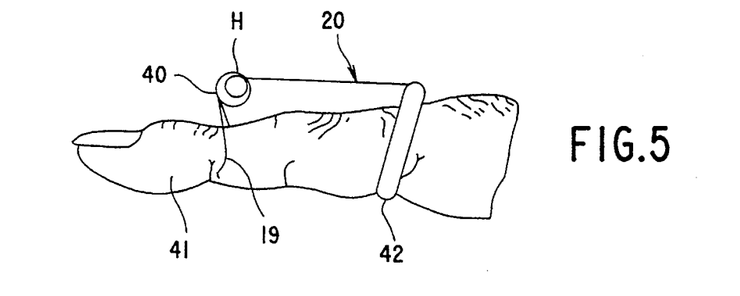
FIG. 5 is a fragmentary, side-elevational view of a mechanical positioner device on a human finger.

As is illustrated in FIG. 5, a human finger 41 is fitted with a mechanical positioner device 20 having a spring 40 fitted with a plastic base 42 at one end and a fork-like holder 19 being activated by the spring 40 at the other end. The forked end 19 is engaged behind the first joint of the finger 41 and the other end 42 is curved around the base of the finger and covered by an insulating softener cushioning device. A suitable repulsion or pushing force of the spring 40 can be achieved by bending it forward or backward at a coil or helix H.

Figure 6:
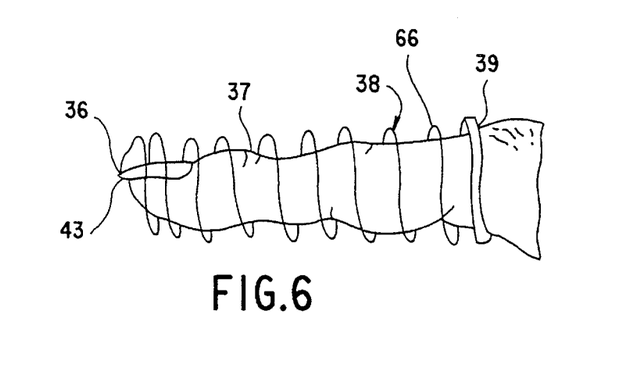
FIG. 6 is a fragmentary, side-elevational view of another mechanical device on a human finger.

FIG. 6 shows a human finger 37 that is fitted with a mechanical positioner device 38 having a plastic cushioning device 39 being curved around the base of the finger 37 and a hooked end 43 of a spring 66 passing through a pierced hole in an over-hanging part of a nail 36. A suitable repulsion of the spring can be achieved by extending or compressing the spring 66.

The installation of such a mechanical positioner is carried out by sliding the spring 66 over the finger 37 to the end, and then inserting the hooked end of the spring 66 into the hole in the nail 36.

Figure 7:
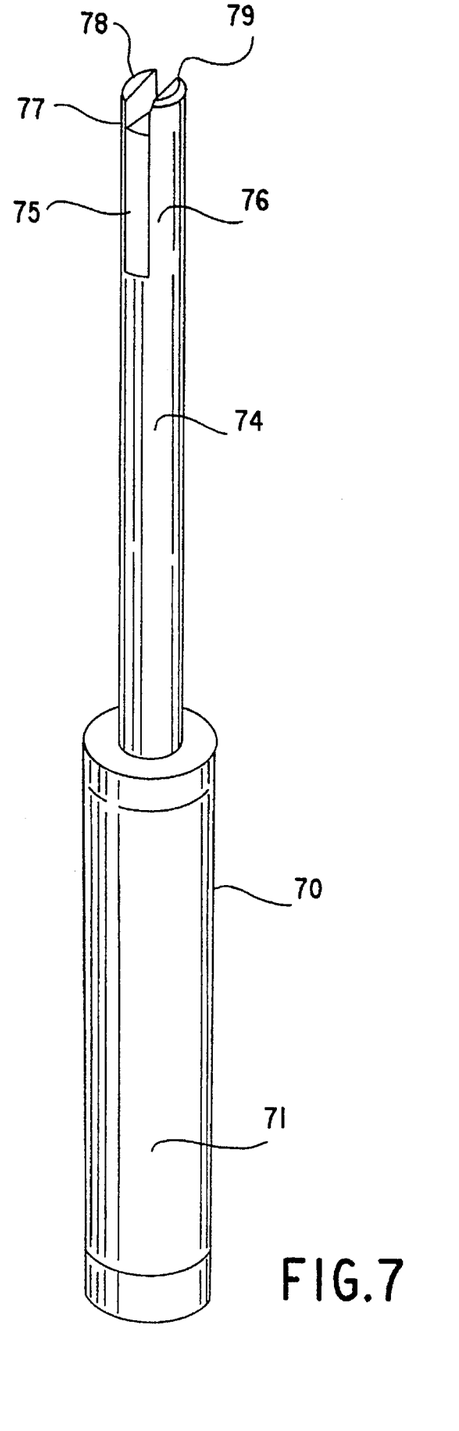
FIG. 7 is an enlarged, perspective view of a magnetic tool.

As is illustrated in FIG. 7, a magnetic tool 70 includes a handle 71 and a magnet 75 mounted in a fork-like notch formed in a rod 74 to provide two magnetic tips 78, 79. The tool tips 78, 79 are applied to rotating magnets for adjusting their rotary position or for unlatching a latch such as a device 90 of FIG. 10, which will be described below.

Figure 8:
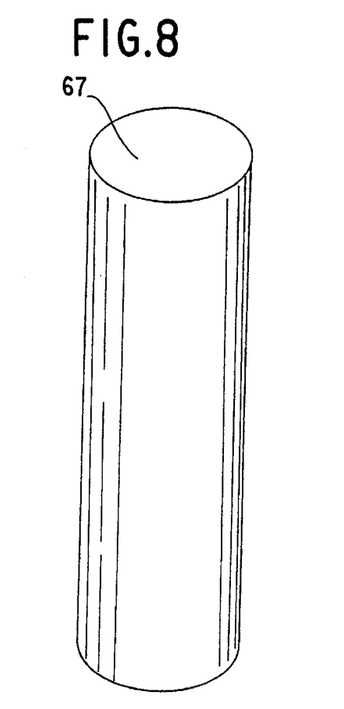
FIG. 8 is a perspective view of a magnetic device.

FIG. 8 illustrates a cylindrically shaped mass of magnetic material 67 which is used in conjunction with any magnet as an implantable target for attraction purposes only, as in FIG. 1C.

Figure 9:
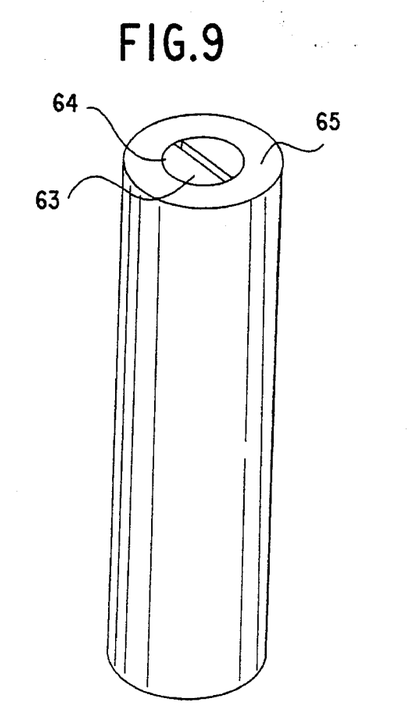
FIG. 9 is a perspective view of a magnetic device with core and sleeve magnets.

As is illustrated in FIG. 9, a cylindrical magnet 64 having a screwdriver slot 63 is rotatably mounted into a magnetic sleeve 65 and is rotatably adjusted by turning with a screwdriver in the slot 63. The cylindrical magnet 64 may also be used for elements 21 and 24 of FIG. 1C. At one given position of the inner or outer magnets 64, 65, they repulse each other by 100%. At a diametrically opposed position, they attract each other by 100%. Any intermediary positions will provide a percentage of their magnetic field attraction or repulsion and consequently a suitable amount of repulsion can be obtained in this way and positioning can be facilitated by marks imprinted on the magnets.

Figure 10:
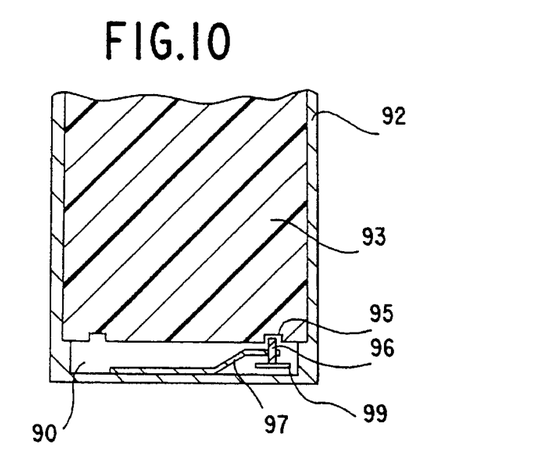
FIG. 10 is a fragmentary, cross-sectional view of a latching device.
Figure 11:
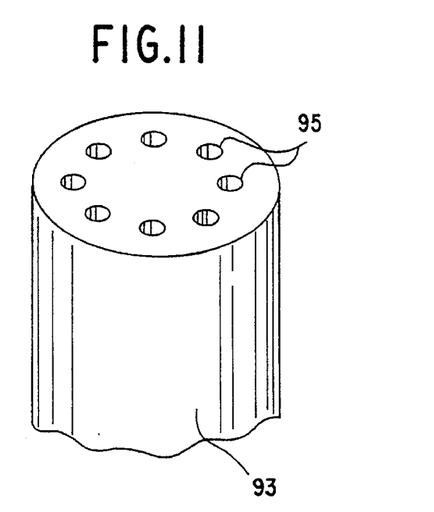
FIG. 11 is a fragmentary, perspective view of a notched magnet bottom.

FIGS. 10 and 11 show a latching magnetic device 90 (which is necessary for keeping the implanted magnets from freely changing their orientation) being installed in the bottom of a container 92, which can be element 44 in FIG. 3. A non-magnetic spring 97 has one end being welded to the bottom of the container 92 and another end being welded on a latch 96. The latch 96 includes a magnetic plateau 99 and is normally lodged in one of several holes 95 that have been formed in the bottom part of a magnet 93, as is shown in FIG. 11. In order to turn the magnet 93, a magnetic tool such as element 70 of FIG. 7 must closely approach the plateau 99 attached to the latch 96. The pull of the magnetic tool 70 will compress the spring 97 and cause the latch 96 to exit completely from the hole 95, freeing the rotation of the magnet 93.

Figure 12:
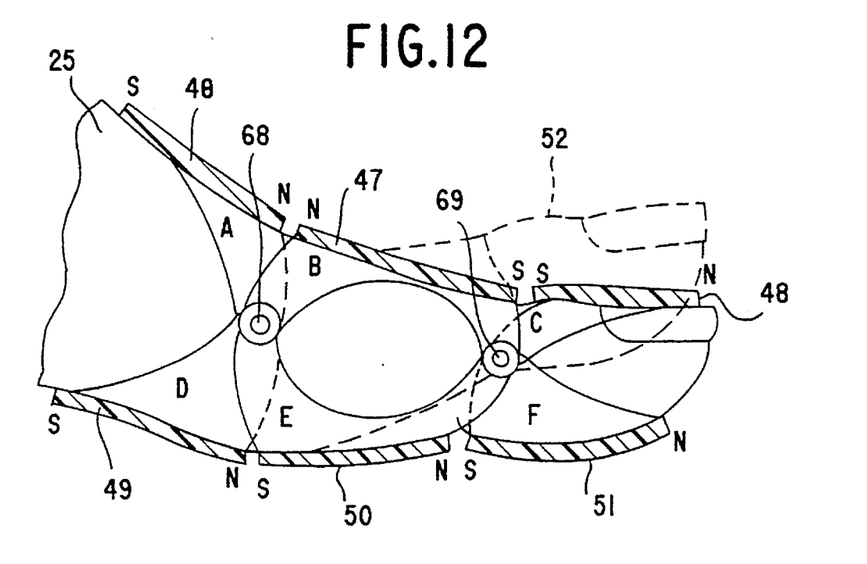
FIG. 12 is a fragmentary, perspective view of a front part of a human foot equipped with a magnetic positioner device.

FIG. 12 illustrates a human foot extremity (metatarsus) 25 which is represented in dotted lines 52 and is a diseased hammer toe, that is fitted with flexible flat magnets 46, 47, 48, 49, 50, 51 which are disposed in such a way as to repulse each other in an upper row and attract each other in a lower row, creating a bending force capable of bringing a part of the foot back into shape and normality. Each of the magnets is fastened to a respective plastic bracket such as brackets A, B, C, D, E, F, which are articulated on axes 68 and 69. In this context, each portion of the foot having a magnet may be considered one respective body part. This device therefore repositions such body parts. The entire toe can also be considered to be a single body part which is shaped by the magnets.

Figure 13:
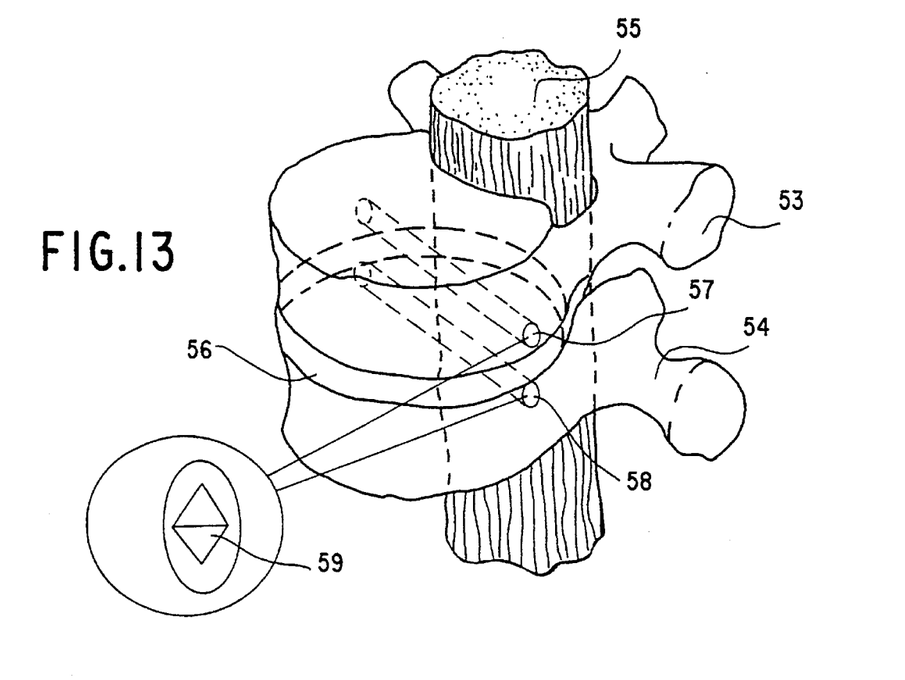
FIG. 13 is a fragmentary, perspective view of human vertebrae equipped with a positioner device.
Figure 14:
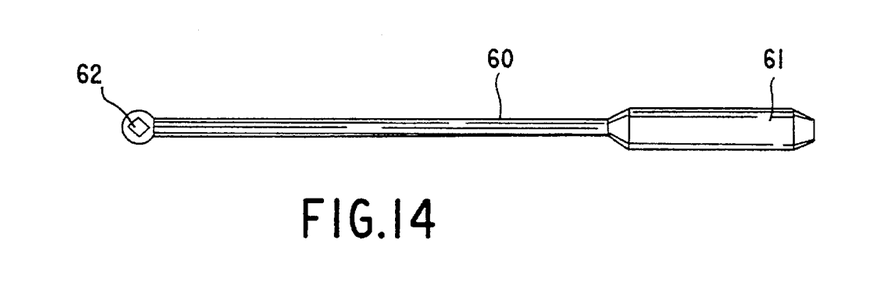
FIG. 14 is an elevational view of a ratchet tool.

As is illustrated in FIG. 13, human vertebrae 53, 54 of a spinal column 55 are fitted with adjustable magnetic positioners 57, 58 having one end 59 made hollow in the form of any geometrical shape, although a square shape is chosen for the hollow end 59, in order to fit a ratchet driver 62 of a wrench 60 in FIG. 14. The wrench 60 has a handle 61 so that it can be used to adjust the magnets 57, 58 to a suitable repulsion according to the positioning therapy of the present invention.

Figure 15:
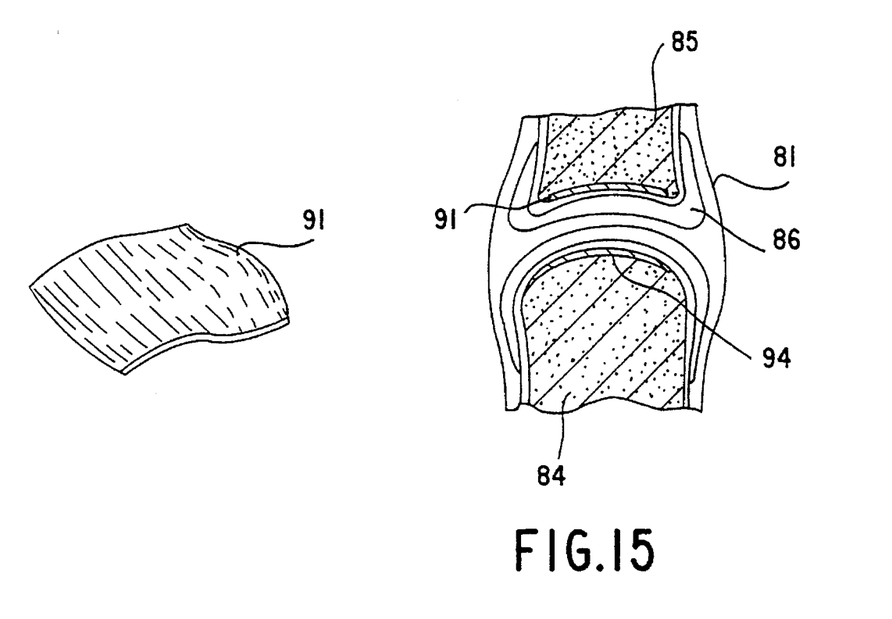
FIG. 15 includes a perspective view of a sheet magnet device and a fragmentary, cross-sectional view of a knee joint in which the sheet magnet device has been implanted.

As is illustrated in FIG. 15, sheet magnets 91, 94 which can be used to make a magnetic positioner are inserted or implanted directly behind the periosteum of bones 84 and 85, in a repulsive position.

Figure 16:
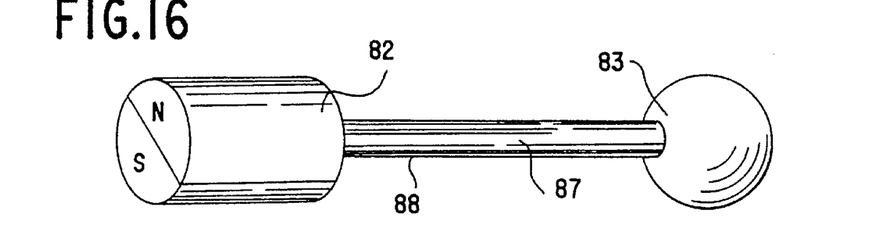
FIG. 16 is a perspective view of a magnetic tool.

FIG. 16 shows a magnetic tool 88, which is made with a rod 87, a handle 83 and a magnet 82 and is used to turn the magnets of the magnetic positioners by magnetic induction, which causes the magnetic positioner to turn when the magnet 82 is rotating in a parallel and close position.

Figure 17:
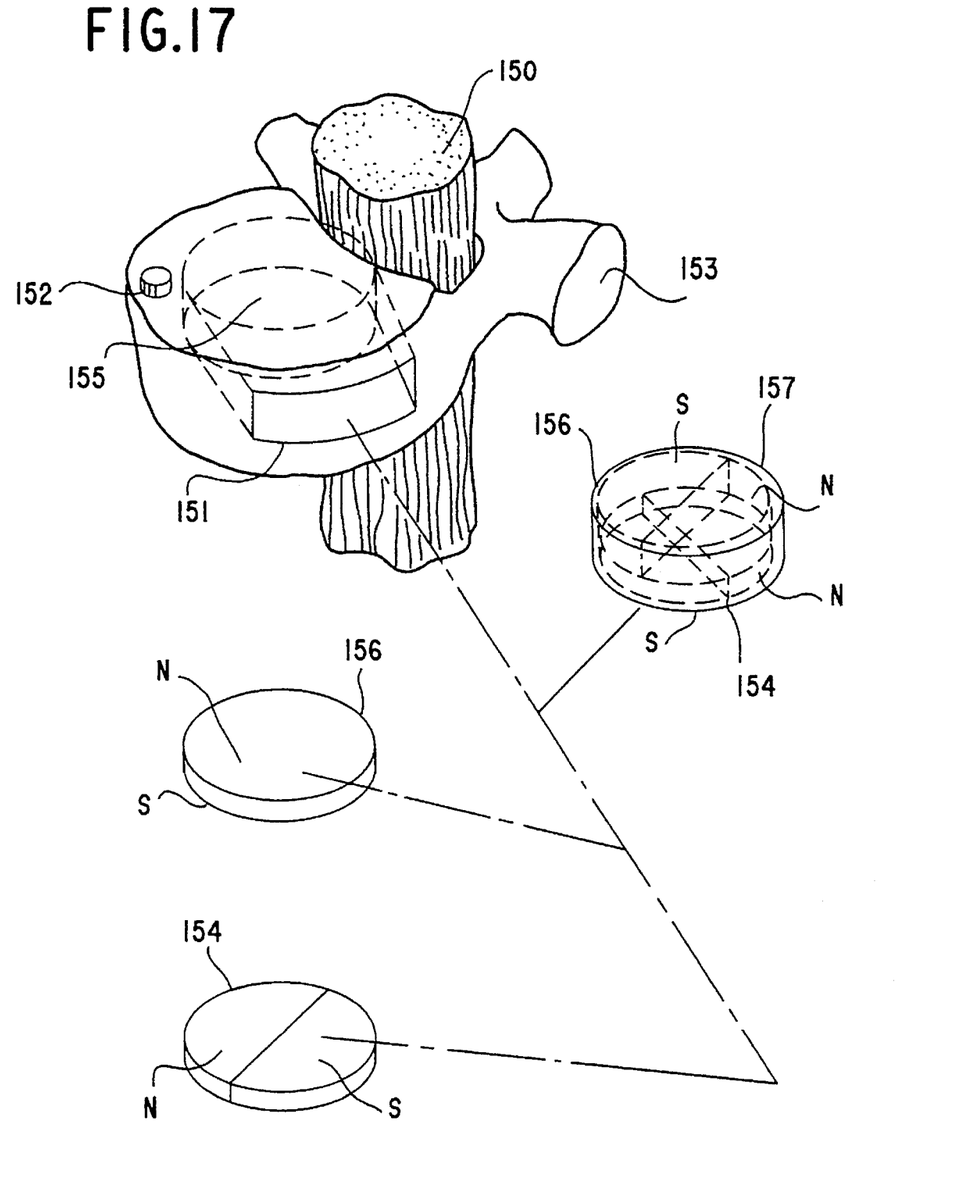
FIG. 17 is a fragmentary, exploded, perspective view of vertebra fitted with a positioner equipped with stacked magnetic disk devices.

As is illustrated in FIG. 17, at least one magnetic device 154, 156 is implanted in an inner chamber 155 in a vertebra 153 of a spinal column 150. The inner chamber 155 is provided with an access passage 151 for this purpose. A flexible bumper 152 is fitted into the vertebra 153.

The function of the implanted magnet devices 154 and/or 156 is as follows:

The vertebra 153 is hollowed out until the inner chamber 155 is formed as is shown in broken lines in FIG. 17. The access passage 151 allows the passage of grinding tools as well as the passage of the disks 154 or 156. Such an inner chamber 155 is partly filled with a suitable cement into which one or more of the magnetic disk 154, 156 are embedded. Then the access passage 151 is filled with cement to conform to the external shape of the vertebra 153.

The number of disks 154, 156 placed inside the vertebra 153 is determined by the size and strength of the magnetic field which is suitable for reaching the desired repulsive or attractive force that is needed.

The stack or pack of magnetic disks, such as the disk 154, may be fixed "in line" with the vertebra 153 in order to produce an "in line" action, or the pack of disks may be fixed in a tilted position, in order to direct the action of the magnetic field in an off-center direction.

In order to avoid a possible striking of two adjacent vertebrae, cushion-like, flexible, soft devices such as the bumper 152 may be affixed on the surfaces of each vertebra, in the way which is represented in FIG. 17.

Every other disk of the pack of magnetic disks, such as the disk 154, that is installed in two or more adjacent vertebrae, must be inverted in order to present like poles for repulsion or unlike poles for attraction. Thus a single vertebra may be a body part that is shaped by the pack of disks.

FIG. 18 shows two self-centering sleeves 159–160 which are depicted as being in line with each other. As an example, the sleeves are constructed in such a way that a bottom part of each implanted sleeve penetrates a top part of the following sleeve. The poles of the sleeves 159 and 160 are disposed in such a way as to be of like polarity when facing each other. When the poles of the two sleeve 159 and 160 are disposed for magnetic repulsion, the sleeves are self centering. The benefit of such a disposition is a permanently centered repulsive force keeping the vertebrae in which they are implanted fully secure against misalignments.

Figure 19A:
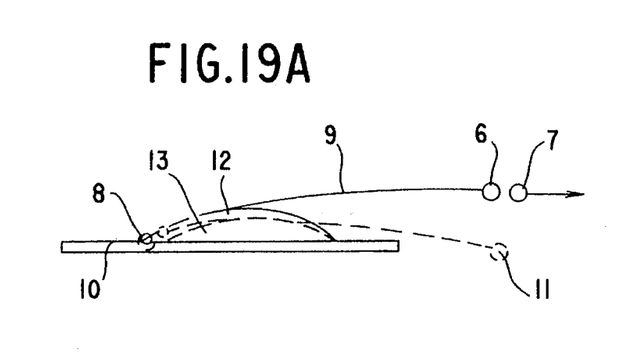
FIG. 19A is side-elevational view of a muscle-controlled positioning device.

As is diagrammatically illustrated in FIG. 19A, a muscle 112 is attached to a bone 110. Such a muscle may be relaxed as is indicated by a broken line 113 or contracted as is indicated by the solid line of the muscle 112. A magnet 106 is attached to an arm 109 having a fulcrum 108. The magnet 106 is in the vicinity of a magnet 107 attached to a body part to be controlled. A relaxed position of the arm 109, which is shown in a broken line, is indicated by reference numeral 111.

Figure 19B:
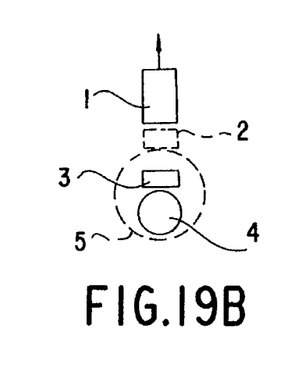
FIG. 19B is an elevational view of another muscle-controlled positioning device.

As is illustrated in FIG. 19B, a muscle 104, shown in a relaxed state, supports a magnet 103. When the muscle 104 is contracted, it has a shape indicated by reference numeral 105 and the supported magnet 103 moves to a location 102, which repulses a magnet 101 attached to a body part to be controlled.

The magnetic tool 70 of FIG. 7 functions as follows. The tool tips 78–79 are placed over the skin of the patient, and specifically over an area where the cylindrical magnet is rotatably fitted into a container, such as the container 44 of FIG. 3. The magnetic field of the tool 70 then engages the magnetic field of the implanted magnet and turning the tool turns the implanted magnet by the same amount and direction.

It is noted that the magnetic tool 70 of FIG. 7 and the magnetic tool 88 of FIG. 16 have been depicted as being of the permanent type for simplicity, but they can be of the electromagnetic type, which allows much more magnetic power to be delivered, providing a more suitable remote control action that can be effected from a more distant location.

The magnetic tool 88 works in the same way as the tool 70, with the difference being that the tool 88 works in a parallel position relative to the rotatable magnet to be adjusted, whereas the magnetic tool 70 works "in line" with the implanted magnet.

It is noted that in any of the embodiments of the apparatus of the invention, the bores or access passages formed in bones or vertebrae, rings around limbs, springs passing through nails, arms attached to muscles or bones, etc., may be considered means for fixing the positioning device in place relative to the body parts, although the invention is not limited to the specific structures which are disclosed and illustrated herein.

It is noted that the special ability of the magnet to engage the magnetic fields together may considerably extend the field of application of the positioning therapy to several other applications by using an external powerful electromagnet in order to:

first, reinforce the power of an implanted magnetic device for a more potent therapy;

second, allow two magnetic implanted devices to repel each other more strongly, creating enough space for passing an endoscope between the two bones, for an improved diagnosis.

I claim:

1. A method for repositioning integral bones to a desired position, which comprises attaching a magnetic positioning device to opposite sides of the integral bones, and adjusting the positioning device for repositioning the bones to the desired position.

2. The method according to claim 1, which comprises performing the attaching step by attaching magnets of the positioning device to the opposite sides of at least two of the bones.

3. The method according to claim 2, which comprises orienting north and south poles of the magnets relative to each other, for repositioning the bones.

4. The method according to claim 2, which comprises placing the magnets into implantable containers, and performing the attaching step by attaching the containers to the bones.

5. The method according to claim 1, which comprises inserting temporarily magnetizable material of the positioning device into the opposite sides of at least two body parts, and approaching the material with a magnetizer, for repositioning the body parts.

6. The method according to claim 1, which comprises attaching magnets of the positioning device to opposite sides of a foot, orienting north and south poles of the magnets towards each other on one side of the foot and away from each other on the other side of the foot, for repositioning the body parts.

7. The method according to claim 1, which comprises implanting sheet magnets at ends of bones in a joint in a mutually repulsive position, for repositioning the body parts.

8. The method according to claim 1, which comprises implanting disk-shaped magnets into chambers formed in adjacent vertebrae in a mutually repulsive position, for repositioning the body parts.

9. The method according to claim 1, which comprises attaching an arm to a bone at a fulcrum, attaching a first magnet to the arm, attaching a second magnet to a body part to be controlled, and placing the magnets near each other, for repositioning the body part.

10. The method according to claim 1, which comprises supporting a first magnet on a muscle, and attaching a second magnet to a body part in the vicinity of the first magnet with like poles of the magnets facing each other, for repulsing the second magnet with the first magnet when the muscle is contracted.

11. The method according to claim 1, which comprises placing magnetic rings over a limb on opposite sides of a joint in the limb, and adjusting relative circumferential positions of the rings causing the rings to attract or repel each other, for repositioning the limb.

12. The method according to claim 1, which comprises placing a base over a limb on one side of a joint in the limb, attaching one end of a spring to the base, attaching another end of the spring to the limb on an opposite side of the joint, and coiling the spring to produce a desired force, for repositioning the limb.

13. The method according to claim 1, which comprises curving one end of a spring around a base of a limb, passing another end of the spring through a nail on the limb, and adjusting coils of the spring around the limb, for repositioning the limb.

14. The method according to claim 1, which comprises performing the attaching step by implanting a positioning device in the form of sleeve-shaped magnets into one of the bones with like poles of the magnets facing each other in a self-centering, mutually repulsive position, for repositioning the bones.

15. A method for repositioning body parts to a desired position, which comprises placing magnets of a positioning device in magnetic sleeves, attaching the magnetic sleeves to opposite sides of at least two body parts, and adjusting the positioning device for repositioning the body parts to the desired position by rotating the magnets in the magnetic sleeves.

16. A method for repositioning body parts to a desired position, which comprises placing magnets of a positioning device into implantable containers, pressing an at least partly magnetic latch into a hole formed in the bottom of one of the magnets with a spring disposed between the bottom of one of the containers and the bottom of the magnet, attaching the containers to opposite sides of at least two body parts, and adjusting the positioning device for repositioning the body parts to the desired position by approaching the latch with a magnetic tool causing the latch to exit the hole and freeing the magnet for rotation.

17. A method for reposition body parts to a desired position, which comprises attaching a positioning device to opposite sides of body parts by implanting rod-shaped magnetic positioners into adjacent vertebrae, and adjusting the positioning device by adjusting the position of the magnetic positioners with a wrench for repositioning the body parts to the desired position.

18. An apparatus for repositioning integral bones to a desired position, comprising a magnetic positioning device to be placed in the vicinity of opposite sides of the integral bones, and means for fixing said positioning device in place relative to the bones, said positioning device being adjustable for repositioning the bones to the desired position.

19. The apparatus according to claim 18, wherein said positioning device includes magnets to be attached to the opposite sides of at least two bones.

20. The apparatus according to claim 19, wherein said magnets have north and south poles being oriented relative to each other, for repositioning the bones.

21. The apparatus according to claim 18, wherein said positioning device includes temporarily magnetizable material being inserted into the opposite sides of at least two body parts, and a magnetizer approaching said material, for repositioning the body parts.

22. The apparatus according to claim 19, wherein said positioning device includes implantable containers surrounding said magnets and being attached to the bones.

23. The apparatus according to claim 18, wherein said positioning device has magnets and brackets fastened to said magnets for attaching said magnets to opposite sides of a foot with north and south poles of said magnets being oriented towards each other on one side of the foot and away from each other on the other side of the foot, for repositioning the body parts.

24. The apparatus according to claim 18, wherein said positioning device includes sheet magnets to be implanted at ends of bones in a joint in a mutually repulsive position, for repositioning the body parts.

25. The apparatus according to claim 18, wherein said positioning device includes disk-shaped magnets to be implanted into chambers formed in adjacent vertebrae in a mutually repulsive position, for repositioning the body parts.

26. The apparatus according to claim 18, wherein said positioning device includes sleeve-shaped magnets to be implanted into one of the bones with like poles of the magnets facing each other in a self-centering, mutually repulsive position, for repositioning the body parts.

27. The apparatus according to claim 18, including an arm to be attached to a bone at a fulcrum, a first magnet attached to said arm, and a second magnet to be attached to a body part to be controlled, said magnets being placed near each other, for repositioning the body part.

28. The apparatus according to claim 18, including a first magnet to be supported on a muscle, and a second magnet to be attached to a body part in the vicinity of said first magnet with like poles of said magnets facing each other, for repulsing said second magnet with said first magnet when the muscle is contracted.

29. The apparatus according to claim 18, including magnetic rings to be placed over a limb on opposite sides of a joint in the limb and circumferentially adjusted in position causing said rings to attract or repel each other, for repositioning the limb.

30. The apparatus according to claim 18, including a base to be placed over a limb on one side of a joint in the limb, a spring having one end attached to said base and another end to be attached to the limb on an opposite side of the joint, said spring being coiled to produce a desired force, for repositioning the limb.

31. The apparatus according to claim 18, including a spring having one end being curved around a base of a limb, another end being passed through a nail on the limb and coils being wrapped around the limb and adjustable, for repositioning the limb.

32. An apparatus for repositioning body parts to a desired position, comprising a positioning device including magnets and magnetic sleeves surrounding said magnets and being attached to opposite sides of at least two body parts, and means for fixing said positioning device in place relative to the body parts, said positioning device being adjustable for repositioning the body parts to the desired position by rotating said magnets in said magnetic sleeves.

33. An apparatus for repositioning body parts to a desired position, comprising a positioning device including magnets, implantable containers surrounding said magnets and being attached to opposite sides of at least two body parts, an at least partly magnetic latch, and a spring disposed between a bottom of one of said containers and a bottom of one of said magnets for pressing said latch into a hole formed in said bottom of said magnet; means for fixing said positioning device in place relative to the body parts; and a magnetic tool causing said latch to exit said hole upon approaching said latch, for freeing said magnet for rotation to adjust said positioning device for repositioning the body parts to the desired position.

34. An apparatus for repositioning body parts to a desired position, comprising a positioning device to be placed in the vicinity of opposite sides of body parts, said positioning device including rod-shaped magnetic positioners to be implanted into adjacent vertebrae, and a wrench for adjusting a position of said magnetic positioners, for repositioning the body parts to the desired position; and means for fixing said positioning device in place relative to the body parts.

35. A method for shaping an integral bone, which comprises attaching a magnetic shaping device to the integral bone, and adjusting the shaping device for modification of the shape of the bone.

36. The method according to claim 35, which comprises placing a magnet of the shaping device along the bone creating an attractive force.

37. The method according to claim 35, which comprises placing magnets of the shaping device at opposite sides of the bone.

38. An apparatus for shaping an integral bone, comprising a magnetic shaping device to be placed in the vicinity of opposite sides of the integral bone to be shaped, and means for fixing said shaping device in place relative to the bone, said shaping device being adjustable for modifying the shape of the bone.

39. The apparatus according to claim 38, wherein said shaping device includes a magnet placed along the bone creating an attractive force.

40. The apparatus according to claim 38, wherein said shaping device includes magnets at opposite sides of the bone.

41. A method for repositioning bones to a desired position, which comprises attaching a positioning device to opposite sides of the bones by implanting magnetic positioners into the bones in the form of adjacent vertebrae, and adjusting the positioning device for repositioning the bones by adjusting the position of the magnetic positioners with a wrench.

42. An apparatus for repositioning bones to a desired position, comprising a positioning device to be placed in the vicinity of opposite sides of the bones, and means for fixing said positioning device in place relative to the bones, said positioning device being adjustable for repositioning the bones to the desired position, said positioning device including magnetic positioners to be implanted into adjacent bones in the form of vertebrae, and a wrench for adjusting a position of said magnetic positioners, for repositioning the bones.

* * * * *